United States Patent [19]

Kruper, Jr.

[11] Patent Number: 4,727,181

[45] Date of Patent: Feb. 23, 1988

[54] PROCESS FOR THE PREPARATION OF α-HALOCINNAMATE ESTERS

[75] Inventor: William J. Kruper, Jr., Sanford, Mich.

[73] Assignee: The Dow Chemical Company, Midland, Mich.

[21] Appl. No.: 854,228

[22] Filed: Apr. 21, 1986

[51] Int. Cl.$^4$ .............................................. C07C 67/00
[52] U.S. Cl. ...................... 560/101; 560/20; 560/21; 560/22; 560/37; 560/42; 560/47; 560/48; 560/55; 560/56; 560/57; 560/100; 560/104; 560/205; 560/219; 562/466; 562/468; 562/471; 562/472; 562/490; 562/491; 562/495; 562/586; 562/588; 562/598
[58] Field of Search ................ 560/55, 56, 57, 20, 560/21, 22, 37, 42, 47, 48, 104, 100, 101, 205, 219; 562/466, 468, 471, 472, 490, 491, 495, 586, 588, 598

[56] References Cited

U.S. PATENT DOCUMENTS

| | | | |
|---|---|---|---|
| 3,313,843 | 4/1967 | Houlihan | 560/104 |
| 3,817,876 | 6/1974 | Fukutani et al. | 562/495 X |
| 3,906,015 | 9/1975 | Mrowca | 260/410.9 R |
| 3,910,958 | 10/1975 | Tsuchihashi et al. | 560/104 X |
| 3,988,358 | 10/1976 | Heck | 560/104 X |
| 4,440,947 | 4/1984 | Arlt | 560/226 |

OTHER PUBLICATIONS

Can. J. Chem., vol. 51, pp. 856–869, (1973), "Studies Relating to Aziridine Antitumor Antibiotics, Part I, Asymmetric Syntheses. Part II. Chiral Aziridines and Their Conversion to α-Aminoacids", J. W. Lown, et al.
Tetrahedron Letters No. 7, pp. 873–876, (1968), "Stereochemistry of the Reaction of Ammonia with Diethyl Bromofumarate and Diethyl Bromomaleate", K. D. Berlin, et al.
Acad. of Sciences, USSR Bull. Div. Chem. Sci., pp. 303–310, (1956), "Allyl Rearrangement in Some Substituted Polyhaloallyl Alcohols", L. I. Zakharkin.
J. Amer. Chem. Soc., vol. 75, pp. 6216–6217, (1953), "The Peroxide-Induced Consensation of Polychloroethylenes with Aromatic Hydrocarbons", L. Schmerling, et al.
Bull. Chem. Soc. Fr., vol. 10, pp. 3846–3855, (1972), "Contribution à l'étude des cétones α,α-diethyléniques polyhalogénées et de Leurs dérivés", F. Pochat, et al.
Nippon Kagaku Zasshi, vol. 78, No. 4, (Apr. 1955), pp. 454–458, "Synthesis of Phenylalanine and beta--Phenylserine from Cinnamic Acid", H. Yukawa, et al.
Heterocyclic Compounds with Three- and Four-Membered Rings, Part One, Interscience Publishers, New York, A. Weissberger. Ed., pp. 535–537, (1964).
Berichte, vol. 53, pp. 1289–1294, (1920), "Über die Siedepunkte der Ester Stereoisomerer Ungesättigter Sáuren", R. Stoermer, et al.
J. Org. Chem., vol. 41, No. 21, pp. 3399–3403 (1976), "Oxidations by Thionyl Chloride.8.A Convenient Synthesis of Benzo[b]thiophenes from Carboxylic Acids and Ketones", T. Higa, et al.
Berichte, vol. 18, pp. 239–241, (1885), "Zur Kenntniss der Monohalogensubstitute der Akrylsäure", R. Otto, et al.
Inorg. Chem. Acta, vol. 3, pp. 255–256, (1969), "Palladium-Catalysed Carbonylation of Unsaturated Compounds", D. Medema, et al.
Chem. Abstracts 54:1333b, "Synthesis of D-D-α-Aminocarboxylic Acids from Compounds Containing the $CCl_2{:}CH$ Group", R. Freĭdlina, et al., (1960).
Chem. Abstracts 71:80972x, "Aromatic Esters of α--Chlorocinnamic Acid", I. Khaskin, et al., (1969).

*Primary Examiner*—Howard T. Mars
*Assistant Examiner*—Vera C. Clarke
*Attorney, Agent, or Firm*—Paul D. Hayhurst

[57] ABSTRACT

Prepare esters of α-halocinnamic acid and related compounds in high yield under relatively mild conditions.

20 Claims, No Drawings

1

PROCESS FOR THE PREPARATION OF α-HALOCINNAMATE ESTERS

BACKGROUND OF THE INVENTION

This invention relates to a process for the preparation of 2-alkenoic acid esters, especially esters of α-halocinnamates.

Typical syntheses of esters of α-halocinnamates involve base-catalyzed eliminations of the cinnamate dihalides such as those reported by Lown et al., *Can. J. Chem.*, 51, pp. 856–59 (1973) and Berlin et al., *Tett. Letts.*, pp. 873–76 (1968). The implementation of this methodology requires esterification of the acid, halogenation of the resultant ester, and base-catalyzed elimination of the isolated dihalide ester (a three-step operation).

The synthesis of α-halocinnamic acids has been demonstrated by Zakharkin, *Acad. Sci. USSR Bull. Div. Chem. Sci.*, pp. 303–10 (1956) and employs an allylic rearrangement of a trichlorovinylphenyl carbinol using an acid catalyst. It is further taught in the art that these carbinol starting materials can be economically produced through the free radical condensation of benzyl alcohol, benzyl chloride or toluene with perchloroethylene. L. Schemerling and J. P. West, *J. Amer. Chem. Soc.*, 75, pp. 6216–7 (1953).

Nonetheless, the known method for rearranging these carbinols leaves much to be desired. For example, the Zakharkin method gives a 4 percent isolated yield of α-chlorocinnamic acid after heating a hydrogen chloride saturation solution of 2,3,3-trichloro-1-phenyl-2-propene-1-ol in acetic acid for 4 hours at 120° C. The difficulty encountered in catalyzing this rearrangement has been noted by others (F. Pochat and E. Levas, *Bull. Chem. Soc. Fr.*, 10, pp. 3846–55 [1972]) who have demonstrated a multistep synthesis of α-chlorocinnamic acid starting from perchloroacrolein. Lastly, the latter two procedures yield the free acid and conversion to the cinnamate ester requires another process operation.

In view of the deficiencies of the prior art, it would be desirable to have a high yield, one-step process for the preparation of α-halocinnamate esters and related compounds which would employ inexpensive starting materials.

SUMMARY OF THE INVENTION

The present invention is such a process comprising contacting in the presence of an acid catalyst a hydroxyl compound and a substituted 1,1-dihalo-1-alkene under reaction conditions such that there is formed a carboxylic acid ester of the formula:

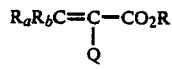

wherein Q is halo, hydrogen, alkyl, haloalkyl, including perhaloalkyl, aromatic or substituted aromatic; $R_a$ and $R_b$ are independently hydrogen or haloalkyl, aromatic, or substituted aromatic; and R is alkyl, haloalkyl, aromatic or substituted aromatic.

The esters of the present invention are useful as chemical intermediates to valuable compounds. For example, it has been demonstrated that specific examples of the esters of the present invention, such as methyl-α-chlorocinnamate, have utility in the synthesis of phenylalanine (H. Yakawa and S. Kimura, *Nippon Kagaku Zasshi*, 78, pp. 454–58 [1955]), an amino acid of commercial importance. Substituted α-halocinnamate esters also serve as good Michael acceptors and have proven utility in the synthesis of aziridine heterocycles of pharmaceutical and antimicrobial interest (P. E. Fanta in "Heterocyclic Compounds", Part A, A. Weissberger Ed., Interscience Publishers, New York, N.Y., pp. 535–37 [1964]).

Surprisingly, the use of certain catalysts and hydroxyl compounds accelerate the present process and give rise to high yields of the desired product under relatively mild conditions.

DETAILED DESCRIPTION OF THE INVENTION

The present invention advantageously employs a 1,1-dihalo-1-alkene, a hydroxyl compound and a catalyst.

Preferred 1,1-dihalo-1-alkenes which can be employed in the process of the present invention are generally represented by the formula:

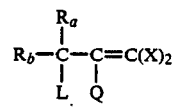

wherein each X is halo; Q, $R_a$ and $R_b$ are as defined hereinabove; and L is a leaving group. Preferably, Q is halo; L is a readily polarizable leaving moiety which can be, for example, halo, hydroxyl, acetates, ethers, esters and the like. Preferably, $R_a$ and $R_b$ are independently hydrogen, perhaloalkyl, aromatic or substituted aromatic. Most preferably, Q is Cl or Br; $R_a$ and $R_b$ are independently phenyl or substituted phenyl; and L is Br or Cl. Examples of 1,1-dihalo-1-alkenes include 3,3-dichloro-2-methyl-1-phenyl-propene-1-ol, 3-bromo-1,1,2-trichloro-3-phenylpropene, 3,4,4-trichloro-1-fluoro-2-(3'-methoxyphenyl)-3-butene-2-ol, 3-O-acetyl-1,1,2-trichloro-3-phenylpropene, 2,3,3-trichloro-1-(4'-chlorophenyl)propene-1-ol, 2,3,3-trichloro-1-(4'-methoxyphenyl)propene-1-ol, 2,3,3-trichloro-1-(4'-nitrophenyl)propene-1-ol, 2,3,3-trichloropropene-1-ol, and 3,3-dichloro-1-phenylpropene-1-ol.

For the purposes of the present invention, the term "substituted aromatic" refers to those substituted aromatic moieties which do not substantially interfere with the desired reaction. Typical examples of substituents are electron donating or electron withdrawing moieties. Examples of preferred substituents for "substituted aromatic" moieties include halo, alkoxy, nitro, sulfhydryl, alkyl, acyl, amino, hydroxy carboalkoxy, and haloalkyl. Examples of more preferred moieties include halo, nitro and alkoxy of up to about 10 carbon atoms.

The hydroxyl compound is an organic compound containing at least one hydroxyl group. Preferred hydroxyl compounds are represented by the formula ROH, wherein R is an aromatic or aliphatic hydrocarbon moiety, preferably of up to about 28 carbon atoms. More preferably, R is alkyl of up to about 10 carbon atoms. Most preferably, R is alkyl of up to about 4 carbon atoms. Any amount of hydroxyl compound which results in the desired product can be employed. Typically, from about 0.5 to about 100 moles of hydroxyl compound is employed per mole of 1,1-dihalo-1-alkene; preferably, from about 2 to about 10 moles per mole is employed. An excess of the hydroxyl compound can be employed as a reaction medium. Examples of typical hydroxyl compounds include methanol, ethanol, isopropanol, n-propanol, n-butanol, 2-butanol, and the like, with ethanol being preferred and methanol most preferred.

A catalyst is advantageously employed in the process of the present invention. The catalyst is a material which increases the rate of the reaction. Acid catalysts are preferred. Sulfuric acid is most preferred. The catalyst is employed in a catalytic amount. Preferably, the catalyst is employed in an amount sufficient to provide from about 0.1 to about 10 equivalents of acidic protons per mole of 1,1-dihalo-1-alkene.

The process can be conducted under any combination of temperature and pressure at which the reaction will proceed. Typically, the temperature ranges from about 70° C. to about 120° C., and preferably is from about 100° C. to 110° C. Most preferably, the reaction is conducted at reflux. The reaction typically is conducted at ambient pressure for the sake of convenience, however, sub- or superatmospheric pressure can be employed if desired. Depending upon the reaction conditions and the reactants employed, a typical reaction is complete in from about 5 minutes to about 1.5 hours.

When the reactants are combined as described hereinabove, a carboxylic acid ester of the following formula is produced:

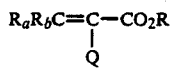

wherein Q, $R_a$, $R_b$ and R are as defined hereinabove. Typically, the ester is produced in a yield of at least about 40 mole percent based on the 1,1-dihalo-1-alkene. Preferably, the ester is produced in a yield of at least about 80 mole percent, more preferably at least about 90 mole percent and most preferably at least about 95 mole percent.

For the purposes of the present invention, the term "yield" refers to the molar amount of isolated product ester divided by the molar amount of 1,1-dihalo-1-alkene starting material employed. The ester product can be recovered from the reaction mixture by known methods such as, for example, extraction, distillation and recrystallization.

SPECIFIC EMBODIMENTS

The following examples are given to illustrate the invention and should not be construed as limiting its scope. All parts and percentages are by weight unless otherwise indicated.

EXAMPLE 1

A solution is prepared using 8 ml of concentrated sulfuric acid and 10 ml of methanol. To the solution is added 3-bromo-1,1,2-trichloro-3-phenyl-1-propene (5.00 g, 16.67 millimoles) with vigorous stirring under a nitrogen atmosphere. The temperature of the mixture is increased to 100° C.-108° C. for 1 hour and a mild reflux occurs. Evolution of hydrogen halide is noted, and analysis of the crude organic portion of the mixture using gas phase chromatography indicates total conversion of the bromide to trans-methyl-α-chlorocinnamate. The reaction mixture is cooled and is extracted with 40 ml of methylene chloride. The organic phase is separated and washed with two 30-ml portions of water, is dried over magnesium sulfate, and is stripped of solvent via rotary evaporation. The resulting light yellow oil is distilled at 92° C.-95° C. and 0.2 mm of mercury using a short path still to give pure trans-methyl-α-chlorocinnamate (3.24 g, 16.5 millimoles) in a yield of 98 mole percent. The spectral and physical properties of this material are in accord with its known structure: 'H NMR (CDCl₃) δ 7.78 (s, 1H vinyl), 7.5-7.75 (m, 2H meta), 7.1-7.4 (m, 3H ortho/para), 3.82 (s, 3H methyl); ¹³C NMR (CDCl₃) δ 163.9, 137.2, 133.1, 130.7, 130.2, 128.5, 121.9, 53.4. B.P. observed=92° C.-95° C. at 0.2 mm Hg; literature=108° C.-109° C. at 0.5 mm Hg. Stoerner, G. and Kirchner, R., Ber. 53, pp. 1289-94 (1920).

EXAMPLES 2-3 AND COMPARATIVE EXPERIMENT 1

The procedure of Example 1 is substantially repeated with exceptions being indicated in Table I.

EXAMPLE 4 p-Methoxyphenyltrichlorovinyl carbinol (2.3 g, 8.6 millimoles) is added to a 40:60 (V/V) solution of sulfuric acid/methanol which is stirred under nitrogen at reflux (100° C.-106° C.) for 7 minutes. Rapid evolution of hydrogen chloride is noted and ceases after this period. The solution is cooled and poured into 40 ml of water, followed by extraction twice with 20 ml of methylene chloride each time. The organic phase is dried over MgSO₄, filtered and rotary evaporated giving z-methyl-2-chloro-3-(4'-methoxyphenyl)propenoate (1.92 g, 8.5 millimoles) in 99 percent yield as a light yellow oil which crystallized on standing (M.P.=68° C.-70° C., M.P.$^{LIT1}$=67° C.-70° C.): 'H NMR (CDCl₃) δ 7.24 (4H, ab quartet), 7.72 (1H, s), 3.76 (3H, s), 3.68 (3H, s); ¹³C NMR (CDCl₃) δ 164.0, 161.1, 136.7, 132.6, 125.4, 119.0, 113.9, 55.2, 53.0.
[1]T. Higa and A. J. Krubsack, J. Org. Chem., 41, pp. 3399-403 (1976).

EXAMPLE 5 p-Chlorophenyltrichlorovinyl carbinol (6.0 g, 22.0 millimoles) is added to a refluxing solution of methanolic sulfuric acid (30 ml as noted in Example 4). Hydrogen chloride evolution is noted during the stirring procedure for 45 minutes. The mixture is cooled and has a workup as in Example 4, which affords z-methyl-2-chloro-3-(4'-chlorophenyl)propenoate (4.7 g, 20.4 millimoles) in 93 percent yield (M.P.=78° C.-80° C.): 'H NMR (CDCl₃) δ 7.77 (1H, s), 7.45 (4H, ab quartet), 3.81 (3H, s); ¹³C NMR (CDCl₃) δ 163.5, 136.1, 135.8, 131.6, 131.3, 128.8, 122.3, 53.4. Analysis calculated for: C, 52.01; H, 3.50. Found: C, 51.85; H, 3.42.

EXAMPLE 6

To a refluxing solution of sulfuric acid (10 ml) and methanol (15 ml) is added 2,3,3-trichloropropene-1-ol (2.00 g, 12.4 millimoles). The mixture is vigorously stirred for 2 hours at 105° C. Aliquots of the organic phase are periodically taken, quenched with water and dried. These are subjected to GC analysis (6¹×⅛ inch nickel with 5 percent OV 225 on 80/100 mesh Anachrom Q at 100° C.-190° C. at 16°/min). After 2 hours, the conversion of starting material is quantitative. Workup as in Example 1 gives 1.1 g of crude methyl-α-chloroacrylate[2] in 74 percent yield. The material is characterized by its GC/MS and 'H NMR data and is noted to contain 10 percent 1,1,2,3-tetrachloropropene.
[2]K. Otto, J. Beckurts, Ber., 18, pp. 239-41 (1885).

The reaction conditions and results of Examples 1-6 are summarized in Table I, for the reaction scheme:

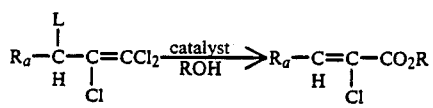

TABLE I

Summary and Comparison of Allylic Rearrangement Conditions

| Run | Substrate $R_a$ | L | (ROH) | Catalyst | Temp. °C. | Time | Mole Percent Isolated Yield |
|---|---|---|---|---|---|---|---|
| Ex. 1 | phenyl | Br | $CH_3OH$ | $H_2SO_4$[1] | 100–108 | 60 min | 98 |
| Ex. 2 | phenyl | OH | $CH_3OH$ | $H_2SO_4$[1] | 100–105 | 20 min | 99 |
| Ex. 3 | phenyl | Br | $CH_3CH_2OH$ | $H_2SO_4$[1] | 100 | 90 min | 80 |
| C.E. 1 | phenyl | OH | HOAc | HCl[2] | 120 | 4 hr | 4 |
| Ex. 4 | p-methoxyphenyl | OH | $CH_3OH$ | $H_2SO_4$[1] | 100–106 | 7 min | 99 |
| Ex. 5 | p-chlorophenyl | OH | $CH_3OH$ | $H_2SO_4$ | 100–106 | 45 min | 92 |
| Ex. 6 | hydrogen | OH | $CH_3OH$ | $H_2SO_4$ | 100–106 | 2 hr | 74 |

[1]40 percent concentrated (98 percent) $H_2SO_4$ in stated solvent
[2]constant boiling HCl/HOAc according to the Zakharkin procedures (L. I. Zakharkin, Acad. Sci. USSR Bull. Div. Chem. Sci., pp. 303–10 [1956])

What is claimed is:

1. A process comprising contacting a hydroxyl compound of the formula ROH, wherein R is an aromatic or aliphatic hydrocarbon moiety, and a 1,1-dihalo-1-alkene in the presence of an acid catalyst under reaction conditions such that there is formed a carboxylic acid ester of the formula:

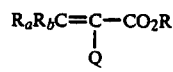

wherein Q is halo, hydrogen, alkyl, haloalkyl, aromatic or substituted aromatic; $R_a$ and $R_b$ are independently hydrogen, haloalkyl, aromatic or substituted aromatic wherein the substituents are electron withdrawing or electron donating moieties; and R is an aromatic or aliphatic hydrocarbon moiety.

2. The process of claim 1 wherein the hydroxyl compound is methanol, ethanol, isopropanol, n-propanol, n-butanol or 2-butanol.

3. The process of claim 1 wherein the acid catalyst is sulfuric acid.

4. The process of claim 3 wherein R contains up to about 28 carbon atoms.

5. The process of claim 4 wherein $R_a$ and $R_b$ are identical.

6. The process of claim 4 wherein R is aliphatic.

7. The process of claim 6 wherein R is alkyl.

8. The process of claim 4 wherein the yield of the carboxylic acid ester is at least about 90 mole percent and R is aliphatic.

9. A process comprising contacting in the presence of an acid catalyst a compound of the formula:

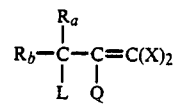

wherein each X is halo; Q is halo, hydrogen, alkyl, haloalkyl, aromatic or substituted aromatic wherein the substituents are electron withdrawing or electron donating moieties; L is a readily polarizable leaving moiety; $R_a$ and $R_b$ are independently hydrogen, haloalkyl, aromatic or substituted aromatic wherein the substituents are electron withdrawing or electron donating moieties; with an alcohol of the formula ROH, wherein R is aromatic or aliphatic, under reaction conditions such that there is formed a compound of the formula:

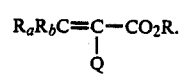

10. The process of claim 9 wherein the acid catalyst is sulfuric acid.

11. The process of claim 10 wherein L is an acetate, an ether, an ester, halo or hydroxyl.

12. The process of claim 11 wherein the yield is at least about 80 mole percent and R is aliphatic.

13. The process of claim 11 wherein the reaction is conducted at reflux temperature.

14. The process of claim 11 wherein Q is halo.

15. The process of claim 11 wherein $R_a$ and $R_b$ are independently aromatic or substituted aromatic.

16. The process of claim 11 wherein Q is Cl or Br.

17. The process of claim 11 wherein R is lower alkyl.

18. The process of claim 11 wherein X and Q are Cl.

19. The process of claim 18 wherein at least one of $R_a$ and $R_b$ is hydrogen, L is bromo or hydroxyl and R is methyl.

20. The process of claim 19 wherein the yield is at least 95 mole percent and L is bromo.

* * * * *